(12) United States Patent
Gozlan et al.

(10) Patent No.: US 10,653,664 B2
(45) Date of Patent: May 19, 2020

(54) ANTIBACTERIAL COMPOSITIONS OF MONO-ALKYL ETHERS OF MONOANHYDRO-HEXITOLS AND ANTIBACTERIAL METHODS USING OF THE SAME

(71) Applicants: Charlotte Gozlan, Villeurbanne (FR); Nicolas Duguet, Villeurbanne (FR); Marc Lemaire, Villeurbanne (FR); Andreas Redl, Aalst (BE)

(72) Inventors: Charlotte Gozlan, Villeurbanne (FR); Nicolas Duguet, Villeurbanne (FR); Marc Lemaire, Villeurbanne (FR); Andreas Redl, Aalst (BE)

(73) Assignee: TEREOS STARCH & SWEETENERS (BE)

( * ) Notice: Subject to any disclaimer, the term of this patent is extended or adjusted under 35 U.S.C. 154(b) by 0 days.

(21) Appl. No.: 16/259,553

(22) Filed: Jan. 28, 2019

(65) Prior Publication Data
US 2019/0224158 A1   Jul. 25, 2019

Related U.S. Application Data

(63) Continuation-in-part of application No. 15/318,662, filed as application No. PCT/IB2015/054418 on Jun. 11, 2015, now Pat. No. 10,221,148.

(30) Foreign Application Priority Data

Jun. 13, 2014   (FR) ...................................... 14 01346

(51) Int. Cl.
| | | |
|---|---|---|
| A01N 43/08 | (2006.01) | |
| A61K 31/341 | (2006.01) | |
| A61K 45/06 | (2006.01) | |
| A01N 43/90 | (2006.01) | |

(52) U.S. Cl.
CPC ............ *A61K 31/341* (2013.01); *A01N 43/08* (2013.01); *A01N 43/90* (2013.01); *A61K 45/06* (2013.01)

(58) Field of Classification Search
CPC ...... A01N 43/08; A61K 31/341; C07H 15/04; C07H 3/10; C07C 43/10
See application file for complete search history.

(56) References Cited

FOREIGN PATENT DOCUMENTS

WO   WO2012/148530 A1   11/2012

OTHER PUBLICATIONS

International Search Report dated Jul. 28, 2015.

*Primary Examiner* — Theodore R. West
(74) *Attorney, Agent, or Firm* — Fresh IP PLC; Aubrey Y Chen

(57) ABSTRACT

The invention relates to an antimicrobial composition of monoanhydro-hexitol monoalkyl ether isomers bearing an alkyl ether radical (OR) at C-3, C-5 or C-6 of the monoanhydro-hexitol, in which the alkyl group (R) is a linear or branched, cyclic or noncyclic hydrocarbon-based group comprising between 4 to 18 carbon atoms. The invention also relates to a method for disinfecting a surface and/or equipment contaminated by bacteria, said method comprising applying to said surface or equipment to be disinfected, a composition according to the invention.

12 Claims, 2 Drawing Sheets

Figure 1:
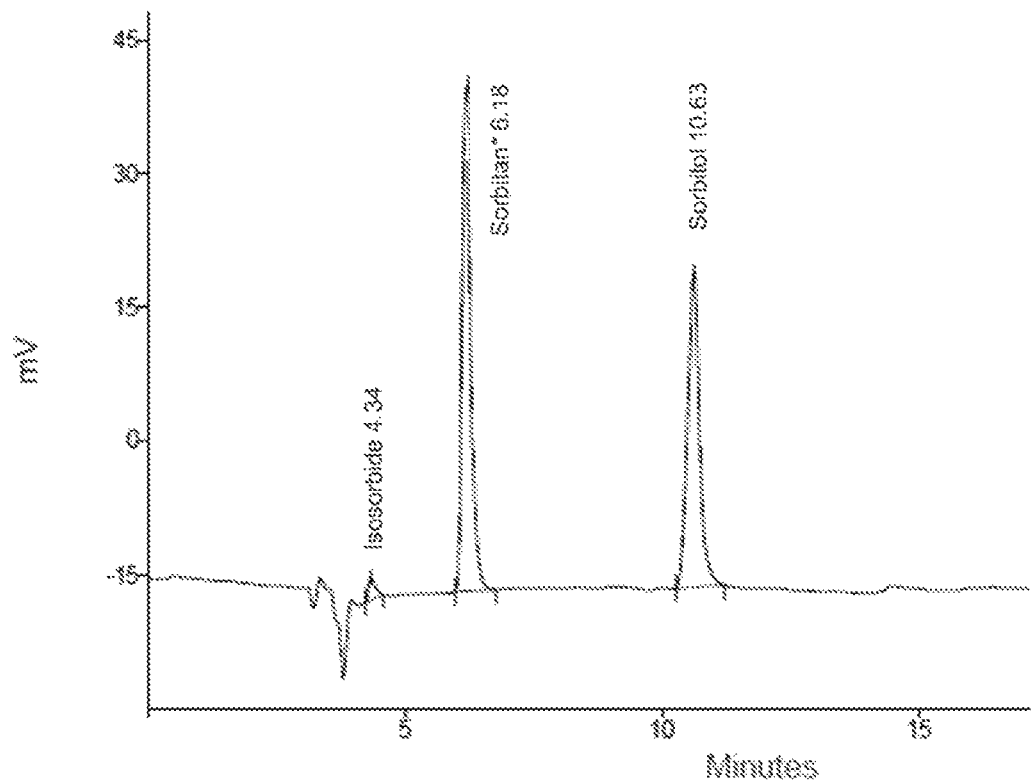

ANTIBACTERIAL COMPOSITIONS OF MONO-ALKYL ETHERS OF MONOANHYDRO-HEXITOLS AND ANTIBACTERIAL METHODS USING OF THE SAME

This application is a Continuation-in-part of U.S. application Ser. No. 15/318,662 filed Dec. 13, 2015, which is a national stage entry of PCT/IB2015/054418 filed Jun. 11, 2015 which claims priority to French Patent Application No. 14/01346, filed Jun. 13, 2014, which are hereby incorporated by reference in their entirety.

The present invention relates to sugar-based monoalkyl ether compositions, and to a process for obtaining such ethers.

In the scientific and technical literature, sugar-based surfactant molecules are well known. Among them, fatty acid esters of sucrose, sorbitan esters and long-chain alkyl polyglucosides have been widely used in food, personal care and cosmetic or pharmaceutical applications. Some of these surfactants have also been widely used as domestic or industrial cleaning agents or as lubricants.

Despite their widespread use and acceptance, it is well known that ester-based surfactants are only stable over a limited pH range, while alkyl glucosides are stable under alkaline and neutral conditions, but not under strongly acidic conditions.

Other drawbacks are associated with the processes used for obtaining these derivatives. Specifically, in the case of long-chain higher alkyl glucosides, trans-glycosylation is necessary. The use of relatively complicated and expensive facilities is necessary in order to obtain a sufficiently pure product. In the case of sugar-based esters, especially sorbitan esters, expensive and toxic solvents are needed, or high reaction temperatures are then necessary to obtain the products in a sufficiently high yield.

In order to improve the stability under acidic conditions of sugar-based surfactant compounds, a sugar alcohol ether has recently been proposed in WO 2012/148530. This patent application describes a process for preparing polyol ethers in the course of which a mass of molten polyols is reacted with a long-chain alkyl aldehyde under reductive alkylation conditions and acid catalysis. According to this disclosure, difficult and extreme reaction conditions are required, in combination with high-pressure equipment in order to achieve the reductive alkylation reaction. In order to obtain the desired products, an excess of sugar alcohol is judged to be necessary relative to the aldehyde. This leads to large energy consumption per mole of sugar alcohol ether. In addition, at the end of each synthesis, the authors identified by $^{13}$C NMR the only compound synthesized (a single regioisomer with an alkyl chain in position 6), for example 2-(2-heptyloxy-1-hydroxyethyl)tetrahydrofuran-3,4-diol (Example 1), 2-(2-hexyloxy-1-hydroxyethyl)tetrahydrofuran-3,4-diol (Example 2) and 2-(2-octyloxy-1-hydroxyethyl)tetrahydrofuran-3,4-diol (Example 3).

Moreover, the prior art describes methods for obtaining monoanhydro-sorbitol. Thus, a method in which sorbitol is dissolved in water in the presence of an acid catalyst and heated under atmospheric conditions for a time sufficient to obtain the maximum content of 1,4-sorbitan is described in *Acta Chemical Scandinavica B* (1981) page 441-449. Similar processes were also disclosed in which the reaction is performed under reduced pressure (U.S. Pat. No. 2,390,395 and US 2007/173 651) or under moderate hydrogen pressure (US 2007/173 654). In patent application US 2007/173 654, a noble metal cocatalyst is used. However, the isosorbide concentrations measured are quite high, in comparison with the 1,4-sorbitan. Thus, the prior art methods do not make it possible to observe a high yield for the production of monoanhydro-sorbitol under mild reaction conditions.

Thus, it is clear that there is a need to propose sugar alcohol ethers, with surfactant properties, which may be obtained via processes in high yield and which are environmentally acceptable, advantageous in terms of energy consumption and also industrially easy to perform.

This need was solved by establishing a composition of monoanhydro-hexitol monoalkyl ether isomers bearing an alkyl ether radical (OR) in position C-3, C-5 or C-6 of the monoanhydro-hexitol, in which the alkyl group (R) is a linear or branched hydrocarbon-based group comprising between 4 to 18 carbon atoms, preferentially between 8 and 12 carbon atoms.

The term "alkyl ether radical (OR) in position C-3, C-5 or C-6" means an alkoxy radical substituting a hydroxyl group (OH) borne by a carbon atom located in position 3, 5 or 6 of the monoanhydro-hexitol.

The expression "monoanhydro-hexitol monoalkyl ether isomers bearing an alkyl ether radical (OR) in position C-3, C-5 or C-6 of the monoanhydro-hexitol" or "isomers in position C-3, C-5 or C-6 of monoanhydro-hexitol monoalkyl ethers" means 3-alkyl monoanhydro-hexitol, 5-alkyl monoanhydro-hexitol and 6-alkyl monoanhydro-hexitol.

Examples of alkyl groups that may be mentioned include butyl, pentyl, hexyl, heptyl, octyl, nonyl, decyl, undecyl and dodecyl groups. Typically, the alkyl group is chosen from octyl, decyl and dodecyl groups.

More particularly, the composition according to the invention comprises at least 1%, 2%, 5%, 10% or 15% (w/w) of any one of the monoanhydro-hexitol monoalkyl ether isomers. Advantageously, the major isomer is 6-alkyl monoanhydro-hexitol. Typically, the 6-alkyl monoanhydro-hexitol isomer represents 34% to 98% (w/w) of the monoanhydro-hexitol monoalkyl ether isomers of the composition according to the invention, preferentially 40% to 80% (w/w), more preferentially 45% to 70% (w/w). 3-Alkyl monoanhydro-hexitol and 5-alkyl monoanhydro-hexitol may be in identical or different proportions and, independently of each other, may represent between 1% to 33% (w/w), preferentially 5% to 30% and more preferentially 10% to 27% (w/w) of the monoanhydro-hexitol monoalkyl ether isomers of the composition.

Preferentially, the ratio [(3-alkyl monoanhydro-hexitol+5-alkyl monoanhydro-hexitol)/6-alkyl monoanhydro-hexitol] is between 0.02 and 2, preferentially between 0.25 and 1.8, more preferentially between 0.4 and 1.7, between 0.7 and 1.5 or between 0.8 and 1.2.

Preferentially, the composition according to the invention comprises at least 90% (w/w), preferably at least 95% (w/w) of monoanhydro-hexitol monoalkyl ether isomers.

Advantageously, the monoanhydro hexitol is chosen from monoanhydro sorbitol, monoanhydro mannitol, monoanhydro iditol and monoanhydro galactitol. Typically, the monoanhydro hexitol is monoanhydro sorbitol or monoanhydro mannitol.

Typically, the monoanhydro-sorbitol monoalkyl ether isomers may be of formula I in which R1, R2 and R3 are an alkyl group and two hydrogen atoms.

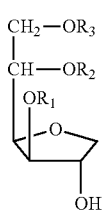

(I)

For example, a C-3 isomer of a monoanhydro-sorbitol alkyl ether (or 3-alkyl monoanhydro-sorbitol) is of formula II in which R1 is an alkyl group.

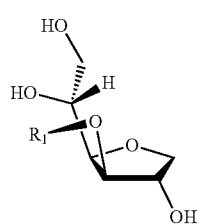

(II)

Preferentially, the C-5 isomer of a monoanhydro-sorbitol alkyl ether (or 5-alkyl monoanhydro-sorbitol) is of formula III in which R2 is an alkyl group.

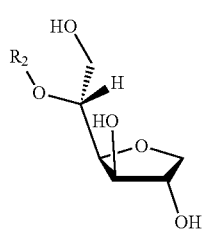

(III)

Preferentially, the C-6 isomer of a monoanhydro-sorbitol alkyl ether (or 6-alkyl monoanhydro-sorbitol) is of formula IV in which R3 is an alkyl group.

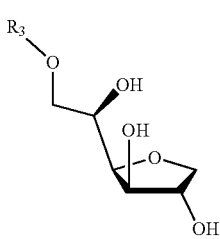

(IV)

In one embodiment, the composition of the invention further comprises at least one antibiotic and/or at least one disinfectant.

The at least one antibiotic may be selected by any one of the antibiotics suitable for external application. In one embodiment, the at least one antibiotic is selected from sulfacetamide sodium, silver sulfadiazine, erythromycin, fusidic acid, bacitracin, neomycin, polymyxin B, gentamycin, mafenide, mupirocin, retapamulin and combinations thereof.

In one embodiment, the at least one disinfectant being selected from formaldehyde, ortho-phthalaldehyde, peracetic acid, hydrogen peroxide, sodium hypochlorite, povidone-iodine, poloxamer-iodine, orthophenylphenol, ortho-benzyl-parachlorophenol, cresols, haxachlorophnene, thymol, pine oil, amylmetacresol, 2,4-dichlorobenzyl alcohol, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide; ethanol, isopropanol, chlorhexidine, silver nitrate, boric acid, dodecanoic acid, lactic acid and combinations thereof.

In one embodiment, the composition further comprises at least one vehicle, preferably the vehicle being a pharmaceutically acceptable excipient.

Examples of suitable excipients include, but are not limited to:

carriers such as water, isopropanol, benzyl alcohol, and propylene glycol;

stiffening agents;

rheology modifiers or thickeners such as carbomers such as, for example, Carbopol®, and polyoxyethylene tallow amines;

surfactants such as anionic, cationic, amphoteric, and non-ionic surfactants, such as, for example, sodium lauryl sulfate, cetostearyl alcohol, cetyl alcohol, magnesium lauryl sulfate, or a combination thereof;

preservatives such as methyl hydroxybenzoate, hydroxybenzoate, butylparaben, ethylparaben, methylparaben, propyl paraben potassium, propyl paraben sodium; parahydroxybenzoate esters; sorbic acid; potassium sorbate; benzoic acid; parabens; chlorobutanol; phenol; thimerosal; sodium benzoate and benzyl alcohol or a combination thereof;

humectants, buffering agents such as sodium hydroxide, citric acid and potassium hydroxide, potassium phosphate or a combination thereof, moisturizing agents and stabilizers.

According to the present invention, "Pharmaceutically acceptable excipient" designates an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by FDA Office of Biologics standards.

In one embodiment, the composition according to the invention is formulated in the pharmaceutical form of:

aqueous solutions, sprays, gels, preferably hydrogels, liquid soap formulations, or oil-in-water emulsions.

In one embodiment, the composition of the invention further comprises at least one non-ionic surfactant such as for example, monolaurine, sorbitan esters such as sorbitan monostearate (Span 60®), sorbitan monolaurate (Span 20®), sorbitan tristearate (Span 65®), polysorbates (Tween®) or a mixture thereof.

The present invention also relates to a process for obtaining a composition of monoanhydro-hexitol monoalkyl ether isomers bearing an alkyl ether radical (OR) in position C-3, C-5 or C-6 of the monoanhydro-hexitol, in which the alkyl group (R) comprises 4 to 18 carbon atoms according to the invention, said process comprising the following steps:

dehydration of a hexitol to obtain a monoanhydro-hexitol substrate;

production of a hexitan alkyl acetal by acetalization or trans-acetalization of the monoanhydro-hexitol substrate obtained, with an aliphatic aldehyde reagent comprising from 4 to 18 carbon atoms, by acetalization, preferentially in a substrate/reagent ratio of between 5/1 and 1/1, or a derivative of an aliphatic aldehyde reagent comprising from 4 to 18 carbon atoms, by trans-acetalization, preferentially, in a substrate/reagent ratio of between 1/1 and 1/3, catalytic hydrogenolysis of the hexitan alkyl acetal, and recovery of a composition of monoanhydro-hexitol monoalkyl ether isomers bearing an alkyl ether radical (OR) in position C-3, C-5 or C-6 of the monoanhydro-hexitol, in which the alkyl group (R) comprises 4 to 18 carbon atoms.

Typically, the process according to the invention also comprises at least one step of neutralization, and/or of filtration and/of purification after any of the steps a), b) and/or d).

Preferentially, the dehydration step a) is performed by treating hexitol, for example in the form of a molten mass of hexitol, with an acid catalyst.

Typically, step a) is performed under a hydrogen atmosphere preferentially at a pressure of 20 to 50 bar.

Advantageously, step a) is performed at a temperature of between 120 and 170° C., preferentially between 130 and 140° C.

The acetalization or trans-acetalization step b) may be preceded by a step of purification of the monoanhydro-hexitol. The purification may be, for example, a chromatography or crystallization step.

Preferentially, the acetalization or trans-acetalization step b) comprises:

bi) optionally, a first step of preheating the monoanhydro-hexitol substrate, preferentially, to a temperature of between 70 and 130° C., typically between 90 and 110° C.;

bii) a step of adding the aliphatic aldehyde reagent or the aliphatic aldehyde derivative and biii) a step of adding a catalyst, preferentially an acid catalyst.

Typically, the acetalization or trans-acetalization reaction is performed at temperatures of between 70 and 130° C., typically between 75 and 110° C., typically 77 and 110° C. The reaction mixtures are heated to temperatures varying as a function of the reagents and solvents used. Typically, for a C5 or C12 aliphatic aldehyde reagent or aliphatic aldehyde derivative, when the solvent is ethanol, the acetalization or trans-acetalization temperature may be 80° C.; when the acetalization or trans-acetalization is performed in the absence of solvent, the reaction temperature may be 95° C. The reaction time is determined by the degree of conversion reached.

The acid catalysts used in steps a) and b) may be chosen independently from solid or liquid, organic or inorganic acids, solid acids being preferred. In particular, the preferred acids are chosen from para-toluenesulfonic acid, methanesulfonic acid and camphorsulfonic acid (CSA) and sulfonic resins.

During the execution of the acetalization or trans-acetalization reaction with an aliphatic aldehyde reagent or an aliphatic aldehyde derivative, the reaction may be performed with or without solvent. When the reaction is performed in the presence of a solvent, the solvent is preferentially a polar solvent, typically a nonaqueous polar solvent.

During the use of a solvent, it may be chosen from polar aprotic solvents such as dimethylformamide (DMF), dimethyl sulfoxide (DMSO), dimethylacetamide (DMA), acetonitrile ($CH_3CN$), tetrahydrofuran (THF), 2-methyltetrahydrofuran (2Me-THF), cyclopentyl methyl ether (CPME), dibutyl ether (DBE), methyl tert-butyl ether (MTBE) or trimethoxypropane (TMP) or polar protic solvents such as methanol (MeOH), ethanol (EtOH), butanol (BuOH) or isopropanol. Polar protic solvents such as ethanol are particularly advantageous.

The acetalization step b) may be performed with an aliphatic aldehyde reagent, in which the aldehyde reagent contains from 4 to 18 carbon atoms. These aldehydes may be chosen from linear or branched aliphatic aldehydes. In a preferred embodiment, the aliphatic aldehydes contain from 4 to 18 carbon atoms, preferentially 5 to 12 carbon atoms. Certain typical representatives of the aldehydes are: pentanal, hexanal, heptanal, octanal, nonanal, decanal, undecanal and dodecanal.

Extensive experimental studies have made it possible to select conditions that ensure optimum degrees of conversion and yields for the acetalization step b). The best results were obtained when the mole ratio of the substrate to the reagent is between 5/1 and 1/1, preferably between 4/1 and 1/1 and more preferably between 3/1 and 2/1.

The trans-acetalization step b) may be performed in the presence or absence of a solvent so as to obtain sugar-based, long-chain alkyl cyclic acetals.

Typically, when the trans-acetalization step b) is performed in the presence of a solvent, the preferred solvent is the alcohol corresponding to the acetal reagent used.

In the course of the trans-acetalization step b), the derivatives of an aliphatic aldehyde reagent may be the dialkyl acetals of the corresponding aldehydes. The dimethyl acetals and diethyl acetals are preferred.

Extensive experimental studies have made it possible to select conditions which ensure that, during the trans-acetalization reactions, optimum yields and degrees of conversion were obtained when the mole ratio of the substrate to the reagent is between 1/1 and 1/3, and preferably between 2/3 and 2/5. The catalysts used are the same as during the acetalization reactions.

Typically, step c) of hydrogenolysis of the hexitan alkyl acetal may be preceded by a filtration and/or purification step.

The purification may be, for example, a chromatography or crystallization step. Preferentially, purification by chromatography is performed using a nonaqueous polar solvent. For example, the nonaqueous polar solvent is identical to the one used in the hydrogenolysis step c).

Advantageously, the hydrogenolysis step c) is performed at a temperature of between 80° C. and 140° C., preferentially at a pressure of between 15 and 40 bar.

The hydrogenolysis step c) may be performed with or without solvent. When it is performed in the presence of solvents, the solvents may be apolar, for instance heptane or dodecane. However, polar solvents and more particularly nonaqueous aprotic solvents are preferred since, for an equivalent selectivity, they allow better conversion than apolar solvents. Examples of aprotic solvents are, inter alia, without being limiting, trimethoxypropane (TMP), methyl tert-butyl ether (MTBE), THF, 2Me-THF, dibutyl ether (DBE) and cyclopentyl methyl ether (CPME). Preferentially, the aprotic solvent is CPME.

The hydrogenolysis step c) is preferentially performed in a polar aprotic solvent, at a temperature between 80° C. and 140° C. and a pressure between 15 and 40 bar, in the presence of a catalyst suitable for performing hydrogenolysis reactions.

Preferably, the hydrogenolysis step c) is performed in a nonaqueous polar solvent, at a temperature of between 100° C. and 130° C. and/or at a pressure of between 25 and 35 bar.

Typically, step c) is performed in the presence of a suitable catalyst such as a catalyst based on precious metals, or based on metals belonging to the ferrous metals group.

As a guide, a catalyst based on metals belonging to the ferrous metals group may be nickel, cobalt or iron.

Preferably, the hydrogenolysis is performed using a catalyst based on precious metals, such as palladium, rhodium, ruthenium, platinum or iridium.

Typically, the catalyst used in step c) may be attached to a support such as charcoal, alumina or silica. Such a support is, for example, in the form of beads. A catalyst based on palladium attached to charcoal beads (Pd/C) is preferred.

According to the invention, the hexitol such as the one used in step a) is a hydrogenated monosaccharide preferentially chosen from sorbitol, mannitol, iditol and galactitol, and a mixture thereof. Sorbitol and/or mannitol are preferred.

When the hexitol is sorbitol, the monoanhydro-hexitol obtained is 1,4-sorbitan of formula (V).

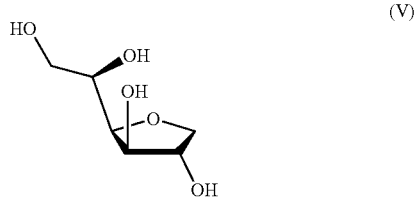

(V)

The inventors have demonstrated that the intermediate product 1,4-sorbitan could be obtained in good yield by treating a molten mass of sorbitol with a solid acid catalyst under a hydrogen atmosphere at a pressure of 20 to 50 bar, at a reaction temperature which may range between 120 and 170° C., for a sufficient period of time so as to obtain an optimum yield of sorbitan. The preferred reaction temperatures are between 130 and 140° C.

The reaction mixture thus obtained is formed from 1,4-sorbitan, unreacted sorbitol, isosorbide and minor amounts of byproducts, as illustrated in the chromatogram represented in FIG. 1. One of the advantages thus observed is the reduction in the level of coloring, in contrast with the standard prior processes.

The dehydration step a) may optionally be followed by a step of purifying the 1,4-sorbitan. Thus, the 1,4-sorbitan is purified from the reaction mixture and the remainder is recycled into the dehydration step. In a particular embodiment, the 1,4-sorbitan is recovered and purified by crystallization. In another preferred embodiment, the 1,4-sorbitan is recovered and purified by chromatography. This purified 1,4-sorbitan is preferably used as substrate for the acetalization reaction.

When the acetalization step b) is performed without solvent, the 1,4-sorbitan is first heated to between 90 and 110° C., and the aldehyde reagent is then added slowly, followed by addition of the catalyst.

Figure 2:
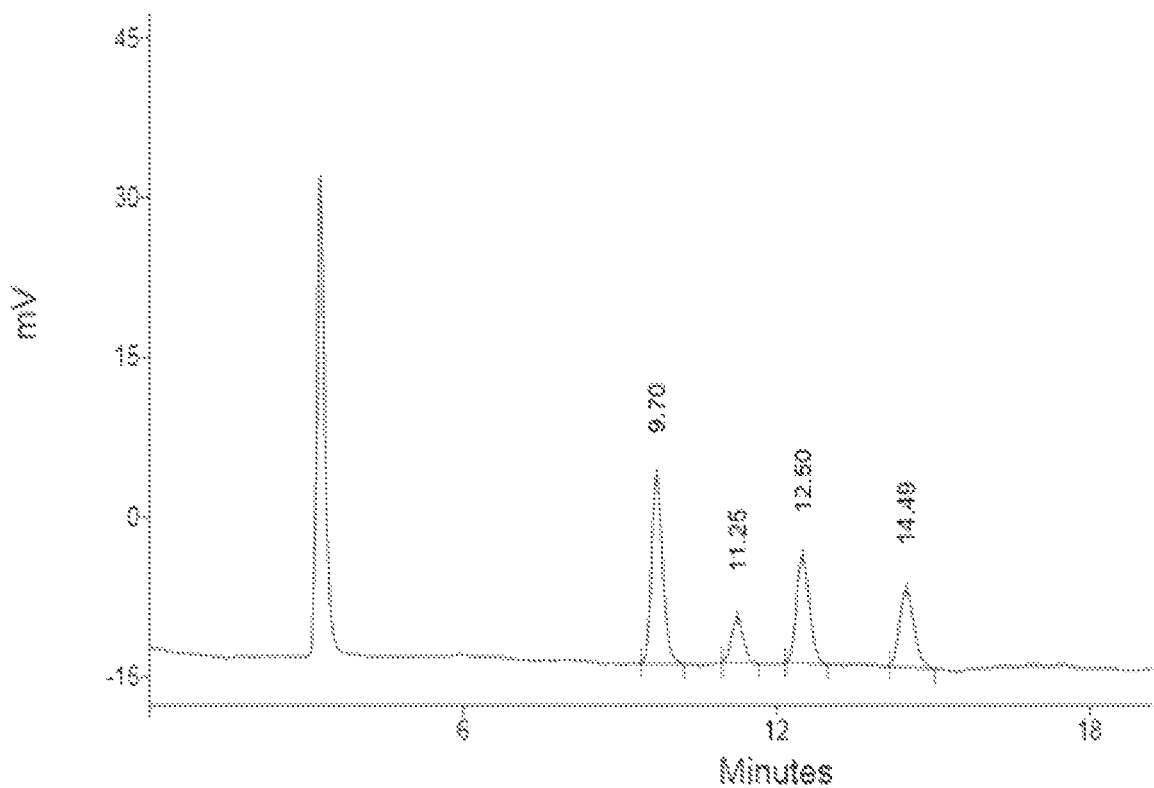

The sorbitan acetal compositions obtained via the processes described above are composed of 4 isomers. This is illustrated in FIG. 2. Two of these isomers correspond to a diastereomeric mixture of 5-membered sorbitan acetal in position 5,6 and the other two isomers correspond to a diastereomeric mixture of a 6-membered sorbitan acetal in position 3,5.

The sorbitan acetals in position 5,6 are of formula VI in which the group R' is an alkyl group. Typically, R' is a linear or branched C3 to C17 aliphatic chain.

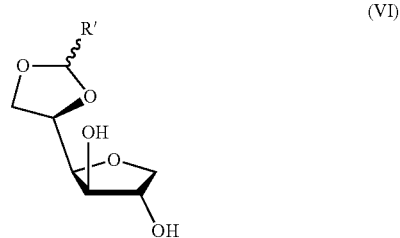

(VI)

The sorbitan acetals in position 3,5 are of formula VII in which the group R is an alkyl group. Typically, R' is a linear or branched C3 to C17 aliphatic chain.

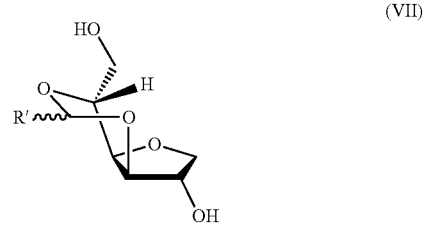

(VII)

The hexitan alkyl acetals obtained above are then subjected to a hydrogenolysis reaction. This acetal mixture may be used after recovery of the crude mixture, or alternatively after chromatographic purification. This hydrogenolysis reaction is performed in a polar aprotic solvent, at a temperature of between 80° C. and 140° C. and a pressure of between 15 and 40 bar, in the presence of a catalyst that is suitable for performing hydrogenolysis reactions.

Preferably, the hydrogenolysis is performed in a nonaqueous polar solvent, at a temperature of between 100° C. and 130° C. and a pressure of between 25 and 35 bar.

The nonaqueous polar solvent CPME (cyclopentyl methyl ether) proved to be particularly advantageous in the hydrogenolysis reaction of the 5,6 and 3,5 cyclic acetals of sorbitan.

The invention also relates to the product obtained by performing the process.

The invention furthermore relates to the use of the composition according to the invention as a nonionic surfactant, emulsifier, lubricant, antimicrobial agent or dispersant. Typically, the composition according to the invention may be used in a food or non-food product or in a pharmaceutical or cosmetic product.

When the composition according to the invention is used as a nonionic surfactant, dispersant or emulsifier, the food product may be chosen from aerated products such as mousses, ice cream, or non-aerated products such as spreading fats or vinaigrettes.

The food product may be in the form of a liquid product chosen from the group formed by sauces, soups and drinks.

Preferentially, C10-C12 alkyl groups are preferred for their use as antimicrobial agent or nonionic surfactant.

Preferentially, C5-C8 alkyl groups are preferred in the use as emulsifier, lubricant or dispersant.

Without limiting the scope of the invention, the invention will now be illustrated further with the aid of a certain number of examples describing the methods for preparing these derivatives.

Alternatively, the invention relates to an antimicrobial composition of monoanhydro-hexitol monoalkyl ether isomers bearing an alkyl ether radical (OR) in position C-3, C-5 or C-6 of the monoanhydro-hexitol, in which the alkyl group (R) is a linear or branched hydrocarbon-based group comprising between 4 to 18 carbon atoms, preferentially from 8 to 12 carbon atoms.

In one embodiment, the alkyl group (R) is a linear or branched hydrocarbon-based group comprising between 10 to 12 carbon atoms.

In one embodiment, the alkyl group (R) is a linear or branched hydrocarbon-based group comprising 10, 11 or 12 carbon atoms. In one embodiment, the alkyl group (R) is a linear or branched hydrocarbon-based group comprising 11 or 12 carbon atoms. In one embodiment, the alkyl group (R) is a linear or branched hydrocarbon-based group comprising 12 carbon atoms.

The invention additionally relates to a method for disinfection or prevention of bacterial colonization by Gram-positive bacteria of a substrate comprising putting the substrate into contact with a composition according to the invention.

In one embodiment, the method is for disinfecting a surface and/or equipment contaminated by bacteria, said method comprising applying to said surface or equipment to be disinfected, a composition according to the present invention.

Typically, the substrate is any substrate that can be colonized by Gram-positive bacteria and that can transmit the infection to an animal by contact or ingestion.

For example, the substrate may be a food of plant or animal origin or a food composition comprising such foods or an extract of these foods and in particular cereals, fruits, vegetables, meat, fish or offal.

The substrate may also be one or more elements selected from among metals, plastics, glass, concrete or stone. Typically, the composition according to the invention may be used in a food or non-food product or in a pharmaceutical or cosmetic product.

Preferentially the substrate is a utensil, a tool or a device used in the food industry, (cooking utensils, a container, a cold storage system, a refrigerator, cold rooms, etc.) in a hospital environment, such as for example surgical tools or prostheses or for public transit (hand rails, seats, etc.).

The invention also relates to a composition for disinfection, purification, sterilization or purification of surfaces.

In one embodiment, the surface and/or equipment is selected from cooking utensils, food compositions, cosmetic or pharmaceutical preparations, cooking surfaces, cold storage systems, surgical tools, surgical prostheses, hospital surfaces, laboratory surfaces, domestic surfaces and public transport surfaces.

Although having distinct meanings, the terms "comprising", "containing", "including" and "consisting of" have been used interchangeably in the description of the invention, and may be replaced by each other.

In one embodiment, the antimicrobial composition is a bactericidal or bacteriostatic composition. According to the present invention, "disinfectant" designates a composition used to inhibit or prevent the growth of bacteria on human, animal and on inanimate objects. In one embodiment, the disinfectant kills at least 99% of the bacterial population. According to the present invention, "bactericide" designates a composition killing substantially, preferably at least 95%, the bacterial population. According to the present invention, "bacteriostatic" designates a composition inhibiting the growth of the bacterial population.

According to a further aspect, the invention also relates to a composition according to the invention for use in the treatment or prevention of bacterial infections by Gram-positive bacteria.

"Treatment" is understood to mean curative treatment (aiming to at least reduce, eradicate or stop the development of the infection) in a patient. "Prevention" is understood to mean prophylactic treatment (aiming to reduce the risk of the infection appearing) in a patient.

The subject may be a healthy subject or a a patient suffering from a skin or mucosal infection.

The "patient" may be, for example, a human being or a non-human mammal (for example a rodent (mouse, rat), a feline, a dog or a primate) affected by or that could be affected by bacterial infections and in particular Gram-positive bacterial infections. Preferably, the subject is a human.

The expression "Gram-positive" refers to bacteria that are colored dark blue or purple by the Gram stain, by contrast with Gram-negative bacteria that cannot retain the purple stain. The staining technique uses bacteria's membrane and wall characteristics. Typically, the Gram-positive bacteria are bacteria from the phylum of Firmicutes, typically of the class of Bacilli in particular chosen from bacteria of the order of Lactobacillales or Bacillales.

According to one embodiment of the invention, bacteria from the order of Bacillales are chosen from the families Alicyclobacillaceae, Bacillaceae, Caryophanaceae, Listeriaceae, Paenibacillaceae, Pasteuriaceae, Planococcaceae, Sporolactobacillaceae, Staphylococcaceae, Thermoactinomycetacea and Turicibacteraceae.

Typically, bacteria from the Listeriaceae family are for example from the genus Brochothrix or *Listeria* and may be typically, chosen from *L. fleischmannii, L. grayi, L. innocua, L. ivanovii, L. marthii, L. monocytogenes, L. rocourtiae, L. seeligeri, L. weihenstephanensis* and *L. welshimeri.*

When Gram-positive bacteria are bacteria from the Staphylococcaceae family, they are in particular chosen from bacteria from the genus *Staphylococcus, Gemella, Jeotgalicoccus, Macrococcus, Salinicoccus* and *Nosocomiicoccus.*

Bacteria from the genus *Staphylococcus* for example chosen from *S. arlettae, S. agnetis, S. aureus, S. auricularis, S. capitis, S. caprae, S. carnosus, S. caseolyticus, S. chromogenes, S. cohnii, S. condimenti, S. delphini, S. devriesei, S. epidermidis, S equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri* and *S. xylosus.*

According to another embodiment of the invention, bacteria from the order of Lactobacillales are chosen from a family of Aerococcaceae, Carnobacteriaceae, Enterococcaceae, Lactobacillaceae, Leuconostocaceae and Streptococcaceae.

Typically, bacteria from the family of Enterococcaceae are chosen from bacteria from genus *Bavariicoccus, Catellicoccus, Enterococcus, Melissococcus, Pilibacter, Tetragenococcus, Vagococcus*.

Bacteria from genus *Enterococcus* are chosen for example from *E. malodoratus, E. avium, E. durans, E. faecalis, E. faecium, E. gallinarum, E. hirae, E. solitarius*, preferentially, *E. avium, E. durans, E. faecalis* and *E. faecium*.

Bacteria from the genus *Staphylococcus* and more particularly *S. aureus* are responsible for many infections of the skin or mucous membranes such as vaginal or nasal membranes. For example, infections such as folliculitis, abscesses, paronychia, boils, impetigo, infections between the digits, anthrax (staphylococcal anthrax), cellulitis, secondary wound infections, otitis, sinusitis, hidradenitis, infectious mastitis, post-traumatic skin infections or infections on burnt skin.

Bacteria from genus *Enterococcus* and in particular *E. faecalis* are responsible in particular for endocarditis, and infections of the bladder, prostate and epididymis.

The invention also relates to a method for treatment or prevention of a bacterial infection by Gram-positive bacteria, preferentially an infection of the skin or mucous membranes, by administration, preferentially topical, to an individual who needs it, of a therapeutically effective quantity of the composition according to the invention.

In a person infected by a Gram-positive bacterium, "therapeutically effective quantity" is understood to mean sufficient quantity to prevent the infection from changing for the worse, or sufficient to make the infection regress. In a person who is not infected, the "therapeutically effective quantity" is the quantity that is sufficient to protect a person who would come into contact with a Gram-positive bacterium and prevent the occurrence of the infection caused by this Gram-positive bacterium.

In one embodiment, the therapeutically effective quantity or the disinfectant effective amount of monoanhydro-hexitol monoalkyl ether isomers of the invention is at least 0.8% (w/w), in weight relative to the total composition. In one embodiment, the therapeutically effective quantity or the disinfectant effective amount of the monoanhydro-hexitol monoalkyl ether isomers of the invention is at least 1% (w/w), in weight relative to the total composition. In one embodiment, the therapeutically effective quantity or the disinfectant effective amount of the monoanhydro-hexitol monoalkyl ether isomers of the invention is 3.5% (w/w), in weight relative to the total composition. In one embodiment, the therapeutically effective quantity or the disinfectant effective amount of the monoanhydro-hexitol monoalkyl ether isomers of the invention is 4% (w/w), in weight relative to the total composition.

Typically, topical administration is done by applying the composition according to the invention to the skin or mucous membranes.

According to one embodiment, the application of the composition of the invention takes place at least once or at least twice per week.

According to one embodiment, the application of the composition of the invention takes place at least once or at least twice per day.

In one embodiment, the composition, of the invention is to be applied topically, orally, buccally, by injection, by spraying, by topical dispersion of a powder, by ophthalmic instillation, by auricular instillation, by percutaneous administration, parenterally, intraperitoneal, by endoscopy, transdermally, transmucosally, nasally, by inhalation spray, rectally, vaginally, intratracheally, and via an implanted reservoir.

In a preferred embodiment, the composition of the invention is to be topically administered. Examples of formulations adapted to topical administration include, but are not limited to, sprays, eye drops, ear drops, sticks, lipsticks, creams, lotions, ointments, balms, gels, powders, leave-on washes or cleansers and/or the like. In one embodiment, the formulation is a spray. In one embodiment, the formulation is an external powder. In one embodiment, the formulation is eye drops. In one embodiment, the formulation is a cream, preferably a hydrophilic cream. In one embodiment, the formulation is a gel, preferably a hydrogel. In one embodiment, the formulation is a liquid cleanser.

Topical administration characterizes the delivery, administration or application of the complex, the composition, the pharmaceutical composition or the medicament of the invention directly to the site of interest for a localized effect (generally onto one or more exposed or outer surfaces thereof, such as the outermost layer of the epidermis, which is exposed and visually observable), e.g., using hands, fingers or a wide variety of applicators (rollup, roll-on or other stick container, tube container, cotton ball, powder puff, Q-tip, pump, brush, mat, cloth and/or the like). The application may be made, e.g., by laying, placing, rubbing, sweeping, pouring, spreading and/or massaging into, or onto, the skin, or by any other convenient or suitable method. Preferably, topical administration is effected without any significant absorption of components of the composition into the subject's blood stream (to avoid a systemic effect).

In one embodiment, the composition of the invention is a hydrophilic formulation, preferably a gel, a solution or a spray, and is applied onto the skin or the surface to be disinfected in order to completely cover the area to be disinfected.

FIGURES

FIG. 1: represents a chromatogram of the reaction mixture obtained in the course of the dehydration reaction according to Example 1.

FIG. 2: represents a chromatogram of the reaction mixture obtained by trans-acetalization without solvent according to Example 8.

Figure 3:
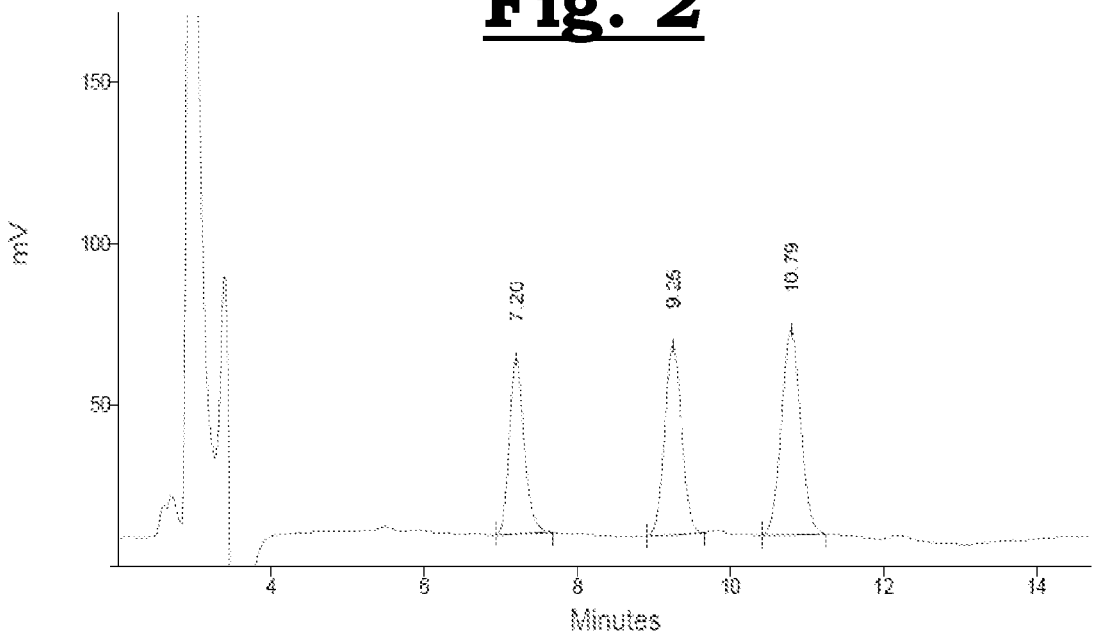

FIG. 3: represents a chromatogram of the reaction mixture obtained by hydrogenolysis according to Example 10.

EXAMPLES

Example 1

Dehydration of Sorbitol:

D-sorbitol (20 g, 110 mmol) and 0.1 mol % of camphorsulfonic acid are added to a 150 mL stainless-steel autoclave. The reactor is hermetically closed, purged three times with hydrogen and hydrogen was then introduced up to a pressure of 50 bar. The system is then heated at 140° C. and stirred with a mechanical stirrer for 15 hours. After cooling to room temperature, the hydrogen pressure was released and the white foam was diluted in ethanol (200 mL) to obtain a homogeneous yellow mixture. The solvent is evaporated off under reduced pressure and the residue is then crystallized from cold methanol and filtered under vacuum. The crystalline material was washed with cold methanol to give 1,4-sorbitan (5.88 g, 35% of theoretical) in the form of a white solid. The purity is >98%, as determined by HPLC, while the crystals showed a melting point of 113-114° C. The degree of conversion of the reaction was determined as 73%, by means of which a mixture of sorbitol, 1,4-sorbitan, isosorbide and a few byproducts in vary limited amount is obtained, such that the 1,4-sorbitan/isosorbide ratio was determined as being 80/20.

Example 2

Acetalization of Sorbitan in DMF:

1,4-Sorbitan (X) (0.5 g, 3 mmol) was dissolved in DMF (1.4 mL) in a sealed tube. Valeraldehyde (Y) (107 µL, 1 mmol) was added dropwise under argon, followed by addition of camphorsulfonic acid (10 mg, 10% w/w), followed by closing the tube. The mixture is heated to 95° C. with magnetic stirring. After 15 hours, the dark reaction mixture was cooled and the solvent evaporated off under reduced pressure. A degree of conversion of 95% was reached. The residue was diluted in ethyl acetate and the excess 1,4-sorbitan was filtered off and washed with ethyl acetate. The filtrate was concentrated under reduced pressure. The residue is purified by flash chromatography (EtOAc/cyclohexane 80/20 to 100/0) to give sorbitan acetal (0.22 g, 89% isolated yield) in the form of a colorless oil. HPLC revealed a mixture of 4 isomers.

Example 3

In this example, various ratios of sorbitan against the aldehyde reagent were tested. The same reaction conditions as in Example 2 were used, but the sorbitan/aldehyde ratio ranged between 1/1 and 3/1. The results are presented in Table 1 below.

TABLE 1

Effect of the sorbitan/aldehyde ratio on the degree of conversion and the isolated yield

| Ratio X/Y | Conversion | Isolated yield (weight %) |
|---|---|---|
| 1/1 | 96% | 62% |
| 2/1 | 81% | 83% |
| 3/1 | 95% | 89% |

The above results show that excess sugar is advantageous in that it can prevent the formation of byproducts such as sugar diacetals. The unreacted sugar may be recovered at the end of the reaction.

Example 4

With a sorbitan/aldehyde ratio of 3/1, various aldehyde reagents were used to give sorbitan acetal reaction products. The same reaction conditions and the same purification steps as in Example 2 were used.
The results are presented in Table 2.

TABLE 2

| Aldehyde | Conversion | Isolated yield |
|---|---|---|
| Hexanal | 100% | 98% |
| Octanal | 89% | 95% |
| Decanal | 69% | 85% |
| Dodecanal | 61% | 80% |

Example 5

Besides the use of DMF as solvent, other solvents were also used to prepare the sorbitan acetal compositions. In this case also, the same reagents were used and the same procedure was followed as in Example 2, except that the reaction temperatures were about 80° C. The results are presented in Table 3.

TABLE 3

| Solvent | Conversion | Isolated yield |
|---|---|---|
| Acetonitrile | 100% | 75% |
| i-PrOH | 97% | 66% |
| DMF | 92% | 92% |

Example 6

Sorbitan Acetalization without Solvent:

1,4-Sorbitan (X) (0.5 g, 3 mmol) was heated to 95° C. in a sealed tube. Valeraldehyde (Y) (107 µL, 1 mmol) was added dropwise, under argon, followed by camphorsulfonic acid (10 mg, 10% w/w), before closing the tube. The mixture is heated to 95° C. with magnetic stirring. After 15 hours, the dark reaction mixture was cooled and diluted in ethyl acetate (2 mL) and the solvent is then evaporated off under reduced pressure. A degree of conversion of 80% was obtained. The residue was again diluted in ethyl acetate and the excess 1,4-sorbitan was filtered off and washed with ethyl acetate. The filtrate was concentrated under reduced pressure. The residue is purified by flash chromatography (EtOAc/cyclohexane 80/20 to 100/0) to give the sorbitan acetal (0.13 g, 54% isolated yield) in the form of a colorless oil. HPLC revealed a mixture of 4 isomers.

Example 7

Trans-Acetalization of Sorbitan in Ethanol:

1,4-Sorbitan (0.5 g, 3 mmol) was dissolved in ethanol (7.5 mL) in a round-bottomed flask and 1,1-diethoxypentane (1.15 mL, 6 mmol) was added under a stream of argon, followed by camphorsulfonic acid (50 mg; 10% w/w). The mixture is heated to 80° C. with magnetic stirring. After 3 hours, the mixture was neutralized and concentrated under reduced pressure. The residue was purified by flash chromatography (ethyl acetate/cyclohexane 80/20 to 100/0) to give the sorbitan acetal (0.43 g, 66% isolated yield) in the form of a colorless oil. HPLC revealed a mixture of 4 isomers.

Example 8

Trans-Acetalization of Sorbitan without Solvent:

1,4-Sorbitan (0.5 g, 3 mmol) and 1,1-diethoxypentane (1,1-DEP) (1.15 mL, 6 mmol) (mole ratio 1/2) were placed in a round-bottomed flask under a stream of argon, followed by camphorsulfonic acid (50 mg; 10 w/w %). The mixture is heated to 80° C. with magnetic stirring. After 3 hours, the mixture was purified directly by flash chromatography (ethyl acetate/cyclohexane 80/20 to 100/0) to give the sorbitan acetal (0.517 g, 73% isolated yield) in the form of a colorless oil. HPLC revealed a mixture of 4 isomers. (FIG. 2)

Example 9

The trans-acetalization reactions without solvent were performed using various mole ratios, various reagents (1,1- dimethoxypentane), various reaction temperatures and various reaction times, the catalyst being the same. Purification of the reaction mixtures was performed by flash chromatography, as in Example 8.

The results are given in Table 4.

TABLE 4

| Reagent | Sorbitan/ reagent ratio | Time (h) | Temperature | Conversion | Isolated yield |
|---------|------------------------|----------|-------------|------------|----------------|
| 1,1-DMP | 1/1 | 15 | 70° C. | 99% | 66% |
| 1,1-DEP | 1/1 | 15 | 70° C. | 81% | 66% |
| 1,1-DEP | 1/1 | 15 | 80° C. | — | 49% |
| 1,1-DEP | 1/2 | 3 | 80° C. | 80% | 73% |

The trans-acetalization reactions starting with 1,1-DMP or 1,1-DEP are particularly pertinent in the reaction without solvent in which sorbitan and 1,1-DEP are in stoichiometric proportions.

Example 10

Hydrogenolysis of Sorbitan Acetals:

Pentylidene-(1,4)-sorbitan (51/49 mixture of regioisomers, 0.98 g, 4.22 mmol) was diluted in dry CPME (30 mL) and placed in a stainless-steel autoclave, with 5% Pd/C catalyst (0.45 g). The reactor is firmly closed and purged three times with hydrogen, and hydrogen is then introduced under pressure (30 bar). The system is heated at 120° C. and stirred for 15 hours. After cooling to room temperature, the hydrogen under pressure is released, the reaction mixture is dissolved in absolute ethanol (100 mL) and filtered (0.01 micron Millipore Durapore filter). The filtrate is evaporated under reduced pressure and the residue is purified by flash chromatography (EtOAc/cyclohexane 90/10 to 100/0, then EtOH/EtOAc 10/90). A mixture of (1,4)-sorbitan pentyl ethers (0.686 g, 69%) was thus obtained in the form of a colorless oil. Analysis by HPLC (C18 column, water/$CH_3CN$ 80/20+0.1% v/v $H_3PO_4$ eluent) showed a 27/33/40 mixture of pentyl(1,4)sorbitan regioisomers in positions 5, 3 and 6. The retention times $R_t$ are 7.20 min (27%), 9.25 min (33%) and 10.79 min (40%) (the peaks having been assigned, respectively, to the regioisomers in positions 5, 3 and 6) (FIG. 3). Spectroscopic data: $^1H$ NMR (400 MHz, $d_6$-DMSO) $\delta_H$ 0.85 (3H, t, J=7), 1.20-1.37 (4H, m), 1.38-1.58 (2H, m), 3.20-3.98 (10H, m, sorbitan protons+$OCH_2$ ethers), 4.02-5.15 (3H, 7m, OH protons); $^{13}C$ NMR (100 MHz, $d_6$-DMSO) $\delta_C$ for major isomer: 13.99 ($CH_3$), 22.01 ($CH_2$), 27.88 ($CH_2$), 28.99 ($CH_2$), 67.50 (CH), 70.59 ($CH_2$), 73.36 ($CH_2$), 73.49 ($CH_2$), 75.66 (CH), 76.37 (CH), 80.34 (CH). $\delta_C$ for minor isomers: 14.02 (2 $CH_3$), 22.03 (2 $CH_2$), 27.86 and 27.91 (2 $CH_2$), 29.21 and 29.55 (2 $CH_2$), 62.02 ($CH_2$), 64.20 ($CH_2$), 68.71 (CH), 69.51 ($CH_2$), 69.79 ($CH_2$), 73.15 ($CH_2$), 73.23 (CH), 73.60 ($CH_2$), 75.53 (CH), 76.45 (CH), 77.37 (CH), 79.28 (CH), 80.10 (CH), 83.95 (CH). HRMS (ESI$^+$) calculated for $C_{11}H_{22}NaO_5$: 257.1363 [M+Na]$^+$; found: 257.1359 (−1.4 ppm).

Example 11

"One-Pot" Synthesis of Sorbitan Ethers from 1,4-Sorbitan:

1,4-Sorbitan (10 g, 62 mmol) is dissolved in dry CPME (30 mL) in a 100 mL round-bottomed flask in the presence of $Na_2SO_4$ (6.5 g, 50 mmol), under an argon atmosphere. Valeraldehyde (3.3 mL, 31 mmol) is added dropwise, followed by Amberlyst 15 (530 mg, 20 w/w % of valeraldehyde). The mixture is heated to 80° C. with magnetic stirring. After 3 hours, the hot mixture is filtered, washed with CPME (2×25 mL) and the filtrate is concentrated under reduced pressure. Without additional purification, the mixture is diluted in CPME (300 mL), dried over $MgSO_4$ and filtered. The filtrate is introduced into a 500 mL stainless-steel autoclave, and 5%-Pd/C (3.3 mg) is added. The reactor is firmly closed and purged three times with hydrogen, and hydrogen is then introduced under pressure (30 bar). The system is heated at 120° C. and stirred for 15 hours. After cooling to room temperature, the hydrogen under pressure is released, the reaction mixture is dissolved in absolute ethanol (250 mL) and filtered (0.01 micron Millipore Durapore filter). The filtrate is evaporated under reduced pressure and the residue (5.8 g) is purified by flash chromatography (EtOAc/cyclohexane 90/10 to 100/0, and then EtOH/EtOAc 10/90). A mixture of (1,4) sorbitan pentyl ethers (3.97 g, 56%) was obtained in the form of a colorless oil (purity >98% by $^1H$ NMR).

Example 12

Octyl-1,4-sorbitan is prepared according to the procedure described in Example 10, starting with octylidene-1,4-sorbitan (39/61 mixture of regioisomers) (5.61 g, 20.4 mmol). The residue is purified by flash chromatography (EtOAc/cyclohexane 80/20 to 100/0 and then EtOH/EtOAc 10/90) to give a mixture of octyl-1,4-sorbitan isomers as a solid white product. Analysis by HPLC (C18 column, water/$CH_3CN$ 80/20+0.1% v/v $H_3PO_4$ eluent) showed a 33/22/45 mixture of regioisomers of octyl(1,4)-sorbitan in positions 5, 3 and 6 (the peaks having been assigned, respectively, to the regioisomers in positions 5, 3 and 6).

Spectroscopic data: $^1H$ NMR (300 MHz, $d_6$-DMSO) $\delta_H$ 0.86 (3H, t, J=7), 1.08-1.39 (10H, m), 1.39-1.58 (2H, m), 3.28-3.95 (10H, m, sorbitan protons+$OCH_2$ ethers), 4.02-5.10 (3H, 7m, OH protons); $^{13}C$ NMR (75 MHz, $d_6$-DMSO): $\delta_C$ for major isomer: 13.98 ($CH_3$), 22.12 ($CH_2$), 25.69 ($CH_2$), 28.73 ($CH_2$), 28.92 ($CH_2$), 29.31 ($CH_2$), 31.29 ($CH_2$), 67.48 (CH), 70.60 ($CH_2$), 73.35 ($CH_2$), 73.48 ($CH_2$), 75.64 (CH), 76.36 (CH), 80.33 (CH) $\delta$C for minor isomers: 13.98 (2 $CH_3$), 22.12 (2 $CH_2$), 25.69 (2 $CH_2$), 28.88 (2 $CH_2$), 28.92 (2 $CH_2$), 28.98 ($CH_2$), 29.52 ($CH_2$), 29.88 ($CH_2$), 31.32 ($CH_2$), 62.00 ($CH_2$), 64.17 ($CH_2$), 68.69 (CH), 69.51 ($CH_2$), 69.82 ($CH_2$), 73.14 ($CH_2$), 73.22 (CH), 73.59 ($CH_2$), 75.53 (CH), 76.44 (CH), 77.37 (CH), 79.27 (CH), 80.07 (CH), 83.94 (CH) HRMS (ESI$^+$) calculated for $C_{14}H_{28}NaO_5$: 299.1829 [M+Na]$^+$; found: 299.1832 (−1.2 ppm)

Example 13

Decyl-1,4-sorbitan is prepared according to the procedure described in Example 10, starting with decylidene-1,4-sorbitan (36/64 mixture of regioisomers) (6.12 g, 20.2 mmol). The residue is purified by flash chromatography (EtOAc/cyclohexane 70/30 to 100/0 and then EtOH/EtOAc 10/90) to give a mixture of decyl-1,4-sorbitan isomers as a solid white product. Analysis by HPLC (C18 column, water/$CH_3CN$ 50/50+0.1% v/v $H_3PO_4$ eluent) showed a 32/16/52 mixture of regioisomers of decyl-(1,4)-sorbitan in positions 5, 3 and 6 (the peaks having been assigned, respectively, to the regioisomers in positions 5, 3 and 6).

Spectroscopic data: $^1H$ NMR (300 MHz, $d_6$-DMSO) $\delta_H$ 0.86 (3H, t, J=7), 1.09-1.38 (14H, m), 1.38-1.58 (2H, m), 3.25-4.01 (10H, m, sorbitan protons+$OCH_2$ ethers), 4.02-5.08 (3H, 7m, OH protons); $^{13}C$ NMR (75 MHz, $d_6$-DMSO) $\delta_C$ for major isomer: 13.98 ($CH_3$), 22.16 ($CH_2$), 25.76

(CH$_2$), 28.79 (CH$_2$), 29.04 (CH$_2$), 29.07 (CH$_2$), 29.14 (CH$_2$), 29.17 (CH$_2$), 29.35 (CH$_2$), 67.53 (CH), 70.63 (CH$_2$), 73.38 (CH$_2$), 73.50 (CH$_2$), 75.69 (CH), 76.40 (CH), 80.35 (CH). $\delta_C$ for minor isomers: 13.98 (2 CH$_3$), 22.16 (2 CH$_2$), 28.98 (2 CH$_2$), 29.01 (2 CH$_2$), 29.14 (2 CH$_2$), 29.17 (2 CH$_2$), 29.35 (2 CH$_2$), 29.57 (2 CH$_2$), 29.92 (2 CH$_2$), 62.01 (CH$_2$), 64.18 (CH$_2$), 68.72 (CH), 69.56 (CH$_2$), 69.84 (CH$_2$), 73.16 (CH$_2$), 73.27 (CH), 73.60 (CH$_2$), 75.56 (CH), 76.48 (CH), 77.41 (CH), 79.30 (CH), 80.08 (CH), 83.96 (CH) HRMS (ESI$^+$) calculated for C$_{16}$H$_{32}$NaO$_5$: 327.2142 [M+Na]$^+$; found: 327.2135 (+2.1 ppm).

Example 14: Measurement of Bacteriostatic Properties of of Sorbitan Ether Derivatives on Gram-Positive Bacteria The bacteriostatic properties of the derivatives are evaluated by measuring their minimum inhibitory concentration (MIC) on the bacteria tested. These measurements are made using the 96-well microplate microdilution method according to the conditions defined below.

Bacteria Tested:

The minimum inhibitory concentrations (MIC) are tested on Gram-positive bacterial strains according to the recommendations of the "Clinical Laboratory Standards Institute" (Clinical-Laboratory-Standards-Institute, 6th ed. Approved standard M100-S17. CLSI, Wayne, Pa., 2007).

The Gram-positive bacteria studied are as follows: *L. monocytogenes* (CIP 103575), *E. faecalis* (ATCC® 29212™) and *S. aureus* (ATCC® 292213 ™).

The Test Compounds of Interest:

The methyl glucopyranoside C5, C6, C8, C10 and C12 ethers (number of carbons on the alkyl chain).

Inoculum Preparation:

The cultures studied, freshly isolated (after incubation on a blood agar at 37° C. for 18 h), are taken up in sterile water (10 mL) until obtaining a 0.5 McFarland (Mc) suspension i.e. 1 to 2×10$^8$ CFU (bacteria)/cm$^3$. The bacterial suspension was then diluted to obtain a final concentration of 5×10$^5$ CFU/cm3.

Preparation of Multiwell Plates for Reading the MIC:

Each well contains an identical quantity of Mueller-Hinton medium (a rich medium for bacterial culture) and bacteria with final 5×10$^5$ CFU/cm3.

The test compounds of interest are solubilized in 2.5% of ethanol before being diluted to different concentrations two by two.

On the multiwell plate, a first series has been planned comprising the culture medium without the test compound of interest. It corresponds to the growth control (control well). These controls serve as reference for comparing bacterial growth with that of the subsequent wells comprising different concentrations of the test compound of interest. The second series of wells comprises the mother solution for the test compound of interest for a concentration in the wells of 4 mM. Each series of wells was diluted two by two until the last series for a final concentration of 0.003 mM. Each concentration is duplicated in the same plate. The plate is incubated for 18 h at 37° C. The reading after incubation shows turbidity in the control wells (revealing bacterial growth). If there is antibacterial activity, the bacterial growth is inhibited, which means that no turbidity or bacterial residue is present. If the test compound inhibits this bacterial growth it may correspond to either bacteriostatic activity in the molecule (inhibits bacterial growth), or to bactericidal activity in the molecule (causes bacteria to die).

Bacterial Count:

To determine whether the agents tested are bactericidal, the minimum bactericidal concentration (MBC) is determined. The MBC corresponds to the concentration leaving a number of bacterial survivors of <4 Log. For this a bacterial count is run from clear wells or without bacterial residue (C≤MIC). To do this, a dilution to 1/100 was conducted with the two wells with the same concentration before seeding on a blood agar using the Spiral technique. After 24 h of incubation at 37° C., the visual count allowed determination of the minimum concentration from which there is no bacterial growth.

The sorbitan C5, C6, C8, C10 and C12 ethers were then tested under the same conditions as previously described and on the same bacterial strains. The results obtained are given in Table 5.

TABLE 5

Antimicrobial results for sorbitan derivatives on Gram positive strains
Minimum inhibitory concentration (MIC) in mmol/L

| Entry | Alkyl chain | Position Ether (Eth) | | |
|---|---|---|---|---|
| | | *L. monocytogenes* | *S. aureus.* | *E. faecalis* |
| 1 | C5 | >4 | >4 | >4 |

33:26:41 isomeric mixture at the 3:5:6 position

TABLE 5-continued

Antimicrobial results for sorbitan derivatives on Gram positive strains
Minimum inhibitory concentration (MIC) in mmol/L

| Entry | Alkyl chain | Position Ether (Eth) | | |
|---|---|---|---|---|
| | | L. monocytogenes | S. aureus. | E. faecalis |
| 2 | C6 | \_/\_/\_/\_O—[sorbitan] 16:33:51 isomeric mixture at the 3:5:6 position | | |
| | | >4 | >4 | >4 |
| 3 | C8 | \_/\_/\_/\_/\_O—[sorbitan] 22:33:45 isomeric mixture at the 3:5:6 position | | |
| | | >4 | >4 | >4 |
| 4 | C10 | \_/\_/\_/\_/\_/\_O—[sorbitan] 16:32:52 isomeric mixture at the 3:5:6 position | | |
| | | >4 | >4 | >4 |
| 5 | C12 | \_/\_/\_/\_/\_/\_/\_O—[sorbitan] 33:27:40 isomeric mixture at the 3:5:6 position | | |
| | | 0.12 | 0.12 | 0.12 |

According to observations on the 96-well microplates, the antimicrobial properties of sorbitan ethers with aliphatic chains less than or equal to 10 carbons could not be observed because all the wells contain turbidity or a bacterial residue. Bacterial inhibition is observed for compounds derived from dodecyl (entry 5).

Example 16: Comparison Tests with Compounds Known in the Prior Art

The activity of sorbitan ether has been compared with that of compounds having similar structures or of a commercial compound like monolaurine (ML) in the table below.

TABLE 7

Comparison of results between reference products and and sorbitan ethers: Minimum inhibitory concentration (MIC) in mmol/L

| Bacteria | Compounds known in the prior art | | | Compound tested EthC12 Sorb |
|---|---|---|---|---|
| | ML 6-EstC12 MeGlu | 6-EthC12 MeGlu pure isomer | | 33:27:40 isomeric mixture at the 3:5:6 position |
| L. monocytogenes. | 0.04 | 0.08 | 0.04 | 0.12 |
| S. aureus | 0.04 | 0.31 | 0.04 | 0.12 |
| E. faecalis | nd | nd | nd | 0.12 |

Example 15: Evaluation of Surfactant and Antimicrobial Properties

All of the products synthesized during the study of physical and chemical properties were tested. These analyses show the different profiles from amphiphilic compounds: hydrotropes and surfactants, and the minimum inhibitory concentrations (MIC) values for each compound on Gram-positive bacteria.

TABLE 6

Comparison results between the critical micelle concentrations (CMC) and the minimum inhibitory concentrations (MIC) in (mmol/L) on the ethers of interest: Minimum inhibitory concentration (MIC) in mmol/L

| Compound | CMC (mM) | MIC (mM) | | |
|---|---|---|---|---|
| | | L. monocytogenes | S. aureus. | E. faecalis |
| 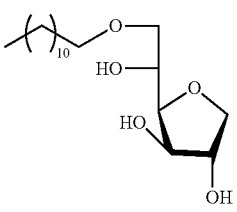 | 0.091 | 0.12 | 0.12 | 0.12 |

According to the results above, it is observed that the C12 methyl glucopyranoside and sorbitan ether derivatives present good results both for their surfactant and antimicrobial properties (on the Gram-positives) because they present low CMC and MIC.

The results obtained demonstrate that the derivatives according to the invention are as effective as monolaurine (ML) since the difference in MIC obtained between the mixtures of EthC12Sorb and monolaurine is low.

Example 16: Measurement of Bacteriostatic Properties of Monosaccharide C12 Ether Derivatives on Gram-Positive Bacteria Since the best results were observed with compounds having a C12 alkyl group, experiments have been conducted on a wider panel of Gram-positive strains with a mixture of compounds obtained according to the previous examples.

The Test Compounds of Interest:
Mixtures of Sorbitan Ethers
3-O-Dodecyl-1,4-D-sorbitan, 5-O-dodecyl-1,4-D-sorbitan and 6-O-dodecyl-1,4-D-sorbitan Inoculum Preparation:
The cultures studied, freshly isolated (after incubation on a blood agar at 37° C. for 18 h), are taken up in sterile water (10 mL) until obtaining a 0.5 McFarland (Mc) suspension i.e. 1 to 1 to $2 \times 10^8$ CFU (bacteria)/cm$^3$. The bacterial suspension was then diluted to obtain a final concentration of $1 \times 10^6$ CFU/cm$^3$.

Preparation of Multiwell Plates for Reading the MIC:
Each well contains an identical quantity of Mueller-Hinton medium (a rich medium for bacterial culture) and bacteria with final [concentration of] $0.5 \times 10^6$ CFU/cm$^3$. The test compounds of interest are solubilized in ethanol or DMSO at 25 mg/mL before being diluted to different concentrations two by two. On the multiwell plate, a first series has been planned comprising the culture medium without the test compound of interest. It corresponds to the growth control (control well). These controls serve as reference for comparing bacterial growth with that of the subsequent wells comprising different concentrations of the test compound of interest. The second series of wells comprises the mother solution for the test compound of interest for a concentration in the wells of 256 mg/L (7 mM). Each series of wells was diluted two by two until the last series for a final concentration of 0.25 mg/L (0.0007 mM). Each concentration is duplicated in the same plate. The plate is incubated for 18 h at 37° C. The reading after incubation shows turbidity in the control wells (revealing bacterial growth). If there is antibacterial activity, the bacterial growth is inhibited, which means that no turbidity or bacterial residue is present.

The minimum inhibitory concentrations (MIC) are tested on Gram-positive bacterial strains according to the recommendations of the "Clinical Laboratory Standards Institute" (Clinical-Laboratory-Standards-Institute, 6th ed. Approved standard M100-S17. CLSI, Wayne, Pa., 2007). The clinical strains have been isolated in the Hospice de Lyon.

The Gram-positive bacteria studied are as follows:

Staphylococci S. aureus: ATCC® 29213™, ATCC 25923,

Staphylococci strains Methicillin-resistant S. aureus (Lac-Deleo USA 300), (MU 3), (HT 2004-0012), LY 199-0053, (HT 2002-0417), (HT 2006-1004), Staphylococci strains Daptomycin-resistant S. aureus (ST 2015-0188), (ST 2014 1288), (ST 2015-0989).

Enterococci: E. faecalis (ATCC® 29212™), clinical enterococci strains E. faecalis isolated from urines: strain 015206179901 (hereinafter 9901), strain 015205261801 (hereinafter 1801)

Enterococci: E. faecium (CIP 103510), clinical strains of Enterococci E. faecium: Van A 0151850763 (hereinafter Van A); strain 015 205731401 (hereinafter 1401), Listeria: L. monocytogenes (CIP 103575), clinical strain isolated from hemoculture (015189074801, LM1), a strain isolated from cerebrospinal liquid (015170199001, LM2), clinical strains isolated from hemoculture (015181840701, LM3).

Inoculum Preparation:

The cultures studied, freshly isolated (after incubation on a blood agar at 37° C. for 18 h), are taken up in sterile water (10 mL) until obtaining a 0.5 McFarland (Mc) suspension i.e. At $10^8$ CFU (bacteria)/$cm^3$. The bacterial suspension was then diluted to obtain a final concentration of $10^6$ CFU/$cm^3$.

Results for the Strains of Genus *Staphylococcus*

TABLE 8

Antimicrobial results from the sorbitan ether on different strains of *Staphylococcus S Aureus*: Minimum inhibitory concentration (MIC) in mg/L

| | *Staphylococcus* | | | | | | | | | |
|---|---|---|---|---|---|---|---|---|---|---|
| | ATCC 25923 | ATCC 29213 | USA 300 | MU 3 | HT 2004-0012 | LY 199-0053 | HT 2002-0417 | HT 2006-1004 | ST 2015 0188 | ST 2014 1288 | ST 2015 0989 |
| C12-Eth-Sorb | 32 | 32 | 32 | 64 | 32 | 32 | 32 | 32 | 64 | 64 | 256 |

Results for the Strains of Genus *Enterococcus*

TABLE 9

Antimicrobial results for sorbitan ether on different *enterococcus* strains. Minimum inhibitory concentration (MIC) in mg/L

| | *Enterococcus* | | | | | |
|---|---|---|---|---|---|---|
| | ATCC29212 | Van A | CIP 103510 | 1401 | 9901 | 1801 |
| C12-Eth-Sorb | 8 | 16 | 16 | 8 | 16 | 8 |

Results or Strains of the *Listeria* Genus

TABLE 10

Antimicrobial results for sorbitan ether on different strains of Listeria. Minimum inhibitory concentration (MIC) in mg/L.

| | Listeria | | | |
|---|---|---|---|---|
| | CIP 103575 | LM1 | LM2 | LM3 |
| C12-Eth-Sorb | 32 | 16 | 32 | 32 |

The invention claimed is:

1. A method for disinfecting a surface and/or equipment contaminated by bacteria, said method comprising applying to said surface or equipment to be disinfected, a composition of monoanhydro-hexitol monoalkyl ether isomers bearing an alkyl ether radical (OR) in position C-3, C-5 or C-6 of the monoanhydro-hexitol, in which the alkyl group (R) is a linear or branched hydrocarbon-based group comprising from 10 to 18 carbon atoms.

2. The method according to claim 1, wherein said bacteria are Gram-positive bacteria.

3. The method according to claim 1, wherein the surface is the skin or the mucosa of a subject in need of being disinfected.

4. The method according to claim 3, wherein the subject is a healthy subject.

5. The method according to claim 3, wherein the subject is a patient suffering from a skin or mucosal infection.

6. The method according to claim 5, wherein the skin or mucosal infection is selected from folliculitis, abscesses, paronychia, boils, impetigo, infections between the digits, anthrax (staphylococcal anthrax), secondary wound infections, otitis, hidradenitis, infectious mastitis, post-traumatic skin infections or infections on burnt skin.

7. The method according to claims claim 1, wherein the surface and/or equipment is selected from cooking utensils, food compositions, cosmetic or pharmaceutical preparations, cooking surfaces, cold storage systems, surgical tools, surgical prostheses, hospital surfaces, laboratory surfaces, domestic surfaces and public transport surfaces.

8. The method according to claim 1, wherein the monoanhydro hexitol is chosen from monoanhydro sorbitol, monoanhydro mannitol, monoanhydro iditol and monoanhydro galactitol and a mixture thereof.

9. The method according to claim 3, wherein the monoanhydro hexitol is chosen from monoanhydro sorbitol or monoanhydro mannitol.

10. The method according to claim 2, wherein the Gram-positive bacteria are bacteria of the genera:
   *Listeria* chosen from *L. fleischmannii, L. grayi, L. innocua, L. ivanovii, L. marthii, L. monocytogenes, L. rocourtiae, L. seeligeri, L. weihenstephanensis* and *L. welshimeri;*
   *Staphylococcus* chosen from *S. arlettae, S. agnetis, S. aureus, S. auricularis, S. capitis, S. caprae, S. carnosus, S. caseolyticus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri* and *S. xylosus;* and
   *Enterococcus* chosen from *E. malodoratus, E. avium, E. durans, E. faecalis, E. faecium, E. gallinarum, E. hirae, E. solitarius, preferentially, E. avium, E. durans, E. faecalis* and *E. faecium.*

11. The method according to claim 1, wherein said composition further comprises at least one antibiotic and/or at least one disinfectant.

12. The method according to claim 11, wherein
   said at least one antibiotic is selected from the group consisting of sulfacetamide sodium, silver sulfadiazine, erythromycin, fusidic acid, bacitracin, neomycin, polymyxin B, gentamycin, mafenide, mupirocin, retapamulin, and combinations thereof; and/or
   said at least one disinfectant is selected from the group consisting of formaldehyde, ortho-phthalaldehyde, peracetic acid, hydrogen peroxide, sodium hypochlorite, povidone-iodine, poloxamer-iodine, orthophenylphenol, ortho-benzyl-parachlorophenol, cresols, haxachlorophnene, thymol, pine oil, amylmetacresol, 2,4-dichlorobenzyl alcohol, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide; ethanol, isopropanol, chlorhexidine, silver nitrate, boric acid, dodecanoic acid, lactic acid, and combinations thereof.

* * * * *